(12) United States Patent
Courvoisier et al.

(10) Patent No.: US 10,470,851 B2
(45) Date of Patent: Nov. 12, 2019

(54) SELF-RETAINING DENTAL SCREW

(71) Applicant: STRAUMANN HOLDING AG, Basel (CH)

(72) Inventors: Stéphane Courvoisier, Basel (CH); Silvio Blumenthal, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 0 days.

(21) Appl. No.: 15/104,270

(22) PCT Filed: Dec. 22, 2014

(86) PCT No.: PCT/EP2014/078953
§ 371 (c)(1),
(2) Date: Jun. 14, 2016

(87) PCT Pub. No.: WO2015/097128
PCT Pub. Date: Jul. 2, 2015

(65) Prior Publication Data
US 2016/0317254 A1 Nov. 3, 2016

(30) Foreign Application Priority Data
Dec. 24, 2013 (EP) .................................... 13006012

(51) Int. Cl.
*A61C 8/00* (2006.01)
*A61C 13/225* (2006.01)

(52) U.S. Cl.
CPC .......... *A61C 8/0068* (2013.01); *A61C 8/0048* (2013.01); *A61C 8/0062* (2013.01); *A61C 13/225* (2013.01)

(58) Field of Classification Search
CPC .... A61C 8/0048; A61C 8/0062; A61C 8/0068
See application file for complete search history.

(56) References Cited

U.S. PATENT DOCUMENTS

| 4,850,870 | A | 7/1989 | Lazzara et al. |
| 5,213,502 | A | 5/1993 | Daftary |

(Continued)

FOREIGN PATENT DOCUMENTS

| EP | 1679049 A1 | 7/2006 |
| WO | 99/16293 A2 | 4/1999 |

(Continued)

OTHER PUBLICATIONS

Mar. 4, 2015 International Search Report issued in International Patent Application No. PCT/EP2014/078953.

*Primary Examiner* — Ralph A Lewis
(74) *Attorney, Agent, or Firm* — Oliff PLC (57) ABSTRACT

A self-retaining screw assembly comprising a dental secondary component and a screw. The secondary component comprises a through passage having an apical and a coronal open end, and a screw seat located between said apical and coronal ends. The screw comprises a screw rod and a screw head, the screw head being dimensioned to abut against the screw seat and the screw rod being dimensioned to pass unhindered through the through passage such that the apical end of the rod can protrude from the apical end of the through passage. The through passage further comprises, coronal of the screw seat, a first section and, directly coronal of the first section a second section having a narrower diameter than the first section, such that the second section forms a restriction in the through passage. The screw head comprises a radially outwardly extending retaining element.

13 Claims, 8 Drawing Sheets

(56) References Cited

U.S. PATENT DOCUMENTS

| | | | |
|---|---|---|---|
| 5,797,741 A | 8/1998 | Bonpard et al. | |
| 5,904,483 A * | 5/1999 | Wade | A61C 8/0048 433/173 |
| 5,947,733 A * | 9/1999 | Sutter | A61C 8/005 433/173 |
| 5,964,591 A * | 10/1999 | Beaty | A61C 8/0001 433/141 |
| 6,159,008 A | 12/2000 | Kumar | |
| 6,986,660 B2 * | 1/2006 | Kumar | A61C 8/005 433/173 |
| 2003/0224330 A1 * | 12/2003 | Aravena | A61C 8/005 433/173 |
| 2010/0203476 A1 * | 8/2010 | Studer | A61C 8/005 433/173 |

FOREIGN PATENT DOCUMENTS

| | | | |
|---|---|---|---|
| WO | 2006/012273 | A1 | 2/2006 |
| WO | 2012/126475 | A1 | 9/2012 |

* cited by examiner

SELF-RETAINING DENTAL SCREW

This invention relates to components comprising a self-retained screw, particularly those used in the dental implant field for attachment to dental implants, such as abutments.

Dental implants are used to replace individual teeth or for anchoring more complex structures, which generally replace several or even all of the teeth. The materials used for dental implants are often titanium and alloys thereof or ceramics, such as zirconia or alumina. These materials have the necessary strength for withstanding the mechanical loads that occur, and they are at the same time sufficiently biocompatible for osseointegration and long term use in the mouth.

Implants have two essential parts: an anchoring part and an abutment part. The anchoring part is embedded in the bone, where it osseointegrates with the bone tissue to provide a firm anchor for the prosthesis. The abutment extends into the oral cavity and provides a support for the prosthesis. The desired prosthetic element (e.g. bridge or crown) is fastened over the abutment such that at least part of the abutment is housed within the prosthesis and provides core support to this. The prosthetic element can be adhesively bonded, cemented, screwed or directly veneered onto the abutment The implant can be constructed in one part, such that the anchoring part and abutment part are produced as one integral, monolithic piece. Hence in such implant systems the integrated anchoring part and abutment are always positioned within the mouth at the same time and the single piece implant extends through the soft tissue into the oral cavity to form a core support for the prosthesis.

However, implants are also often constructed in two or more parts, in which case they consist of at least an anchoring part, often referred to in isolation as the implant, and a separate abutment, sometimes referred to as a spacer or post element. The anchoring part is usually either embedded completely in the bone, that is to say to the height of the alveolar crest, or protrudes by a few millimetres from the alveolar crest into the soft tissue. The abutment is mounted either directly or indirectly to the anchoring part after the latter has become incorporated (osseointegrated) into the bone or directly after the anchoring part has been inserted. It can also be attached to the anchoring part prior to insertion. Most usually the abutment is not mounted until after osseointegration. In such cases a component called a healing cap is often mounted to the implant during the osseointegration process to prevent incursion of soft tissue over the implant site.

In contrast to one piece implants, multi-part implants are more versatile, because the anchoring part and the abutment can be adapted to individual requirements. In particular the abutment shape and angulation, relative to the anchoring part, can be selected after implant insertion. This provides the surgeon with more flexibility and room for error in the placement of the implant. An additional advantage of multi-part implants is that the abutment can be made from a different material than the anchoring part.

Due to their versatility multi-part and particularly two-part dental implants are more commonly used than one-piece implants.

During the lifetime of a dental prosthesis, which can be over 20 years, the implant system will be subjected to large loads caused by mastication. The abutment must therefore be firmly fastened to the implant in order to prevent loosening and potential loss of the component. This can be achieved in numerous ways, for example, via compression fit or gluing.

However, screw fit connections are generally preferred. By applying a sufficiently high torque during attachment a firm connection between the implant and abutment can be achieved.

In many systems therefore the implant comprises an internal threaded bore, while the abutment comprises a corresponding apical thread, thus allowing the abutment to be screwed directly into the implant.

However, this has the disadvantage that the exact angular position of the abutment relative to the implant is not known until final fixation. This can have disadvantages, particularly when the abutment is intended to support a single tooth prosthesis.

Therefore, many multi-part implant systems comprise anti-rotation means, which prevent relative rotation between the implant and abutment and which set a finite number of angular positions which the abutment can have relative to the implant.

These anti-rotation means consist of complementary non-circular symmetric portions in the implant and abutment, usually having a polygonal cross-sectional shape such as a hexagon or octagon.

Such systems ensure that the exact angular position of the abutment in relation to the implant is known prior to fixation and can help to prevent loosening of the abutment during the lifetime of the implant system.

Of course, when such anti-rotation means are employed it is not possible to rotate the abutment relative to the implant and hence the abutment can no longer be directly screwed into the implant. Therefore a third component, often a screw known as a "basal screw", is used to connect the abutment to the implant.

When a basal screw is used the abutment typically comprises a screw channel extending through the abutment and having a screw seat. This enables the basal screw to be fed through the abutment until the underside of the screw head abuts the screw seat and for a screwdriver to be inserted into the channel to engage the screw and fasten this to the internal threaded bore of the implant, thus clamping the abutment securely to the implant.

Examples of such a known implant system can be found for example in EP1679049, in which the screw seat is conical and WO2006/012273, in which the screw seat is planar.

As well as abutments, screws are also used to connect other components to the implant, for example, healing caps, closure screws and impression posts, all of which are well known in the dental implant field.

Dental implants and their related components are necessarily small, in order to fit within the human jaw bone without disturbing neighbouring teeth and to minimise bone removal. Basal screws in particular, which must fit within the implant, are small components and typically have a diameter of approximately 1-2.5 mm and a length of 3-5 mm.

The handling of such small components is tricky and it is not uncommon for these screws to be dropped, which may damage the screw and further requires the screw to be re-sterilised before use. The handling of screws in the operating theatre poses particular challenges and risks, as this must be done using surgical gloves and a dropped screw may result in aspiration of the screw by the patient. The re-sterilisation of dropped screws or the obtaining of a replacement also increases the length of the surgery.

In order to increase the ease of use of such screws, it is known to provide dental components, such as abutments and impression posts, with so called "self-retaining screws", which are loosely held within the dental component.

One example of a self-retaining screw is found in U.S. Pat. No. 5,213,502. Here the screw channel comprises a threaded section, to which the thread of the screw can be fastened. This connects the screw to the component, such that they can be transported and handled as a unit. Once the component has been placed on, or in, the implant the screw is tightened such that it is unfastened from the threads of the screw channel and fastened to the implant threads.

Such systems have the disadvantage that the vibrations experienced during transportation can cause the screwed connection between the screw and component to loosen and for the screw to become detached.

US2010/0203476 and WO99/16293 overcome this problem by providing a support ring, which is inserted into either the coronal or apical end of the screw channel after insertion of the screw. The ring is then welded or otherwise fixed in place. The ring has the effect of narrowing the screw channel, thus preventing the head of screw from passing through the end of the channel into which the ring has been inserted. The screw is thus securely retained within the component, even during transportation.

The creation of such a self-retaining screw is however costly, as an additional element, namely the support ring, must be manufactured and then fixedly connected to the abutment, or other component.

Although the above problems are most usually encountered with respect to multi-part implant systems, similar concerns can also arise in one-part implant systems. Although in these systems the abutment is integral to the anchoring part it can often be desired to attach additional components to the abutment part of the implant, e.g. impression posts or the final prosthesis. Where such components are fixed to the implant using screws the above discussed problems can also occur.

Therefore the present invention concerns both one-part and multi-part implants. For the remainder of this specification therefore, the term "implant" will be used to denote the part of an implant system which in use is anchored within the bone and can refer to a one-piece implant or to the anchoring part of a multipart implant, and the term "secondary component" will be used to denote a component which is, in use, directly or indirectly fastened to the implant. The secondary component can be the abutment of a multi-part implant, which in use extends into the oral cavity and provides core support for a dental prosthesis, or may comprise an auxiliary component which is temporarily fixed to the implant, such as a healing cap or impression post.

It is an object of at least a preferred embodiment of the present invention to provide a self-retaining screw system which securely retains the screw during transportation and which is simple to manufacture and construct.

According to one aspect of the present invention there is provided a self-retaining screw assembly comprising a dental secondary component and a screw, the secondary component comprising a through passage having an apical and a coronal open end, and a screw seat located between said apical and coronal ends, the screw comprising a screw rod and a screw head, the screw head being dimensioned to abut against the screw seat and the screw rod being dimensioned to pass unhindered through the through passage such that the apical end of the rod can protrude from the apical end of the through passage, the through passage further comprising, coronal of the screw seat, a first section and, directly coronal of the first section, a second section having a narrower diameter than the first section, such that the second section forms a restriction in the through passage, and the screw head comprising a radially outwardly extending retaining element, at least one of the restriction and retaining element being a resilient member deformable from a first, rest, position, in which the resilient member has a first diameter, to a second, stressed, position, in which the resilient member has a second diameter, the restriction and the retaining element being dimensioned such that the retaining element can only pass through the restriction when the resilient member is in the stressed position.

In accordance with conventional dental terminology, "apical", refers to the direction towards the bone and "coronal" to the direction towards the teeth. Therefore the apical end of a component is the end which, in use, is directed towards the jaw bone and the coronal end is that which is directed towards the oral cavity.

A resilient member is one whose shape can be distorted or otherwise adjusted but which returns to its original, rest, shape after removal of the distorting force. This quality allows the member to be bent, compressed or otherwise displaced in order to enable relative axial movement between the screw and the secondary component, but then to spring back to, or at least towards, its original position after the retaining element has passed through the restriction, in order to hold the screw within the through passage. Such connections between components are often referred to as "snap connections" due to the springing or snapping of the resilient member back to, or towards, its original shape once the connection has been made. This often provides the user with physical and/or aural feedback that the connection has been made.

The ability of the resilient member to change diameter allows the screw to be placed into the coronal end of the through passage and forced past the restriction. Once the retaining element on the screw head has passed the restriction it cannot be removed from the coronal end of the through passage unless force is again applied to distort the resilient member. At the same time the screw head cannot pass apically beyond the screw seat. The screw is therefore retained within the component.

Because the resilient member must be placed under a sustained, applied force before the retaining element can pass through the restriction, this is not subject to loosening due to the random vibrations experienced during transport, which tend to be relatively brief and sporadic in nature. Unlike a screw connection, in which the threaded connection can be incrementally unwound by such movements, the snap connection of the present invention cannot suffer the same gradual loosening.

Additionally, the resilient nature of the snap connection means that no additional step or part is required after insertion of the screw in order to retain the screw within the component, as is the case with a support ring. This improves the speed and ease of assembly as well as the cost of manufacture.

According to the present invention the retaining element can only pass through the restriction when the resilient member is in a stressed position. In other words, when the resilient member is in its rest position the diameter of the retaining element is greater than the diameter of the restriction, such that the retaining element cannot pass through the restriction. Upon deformation of the resilient member into the stressed position the diameter of the retaining element is less than or equal to the diameter restriction, such that the retaining element can pass through the restriction.

For the avoidance of doubt, by the diameter of the retaining element it is meant the diameter across the screw head at the location of the retaining element.

Either the retaining element or the restriction can be the resilient member and thus be deformable from a first diameter to a second diameter. Preferably, the retaining element is the resilient member. Therefore in such embodiments at least the retaining element is a resilient member deformable from a first, rest, position having a first diameter to a second, stressed, position, having a second diameter, the retaining element and restriction being dimensioned such that the retaining element can only pass through the restriction when in the second position.

It is possible for both the retaining element and restriction to be resilient members, such that both must distort to a stressed position in order to enable passage of the retaining element past the restriction. However, it is preferable that only one of these features is resilient, the other forming a rigid structure with a fixed diameter. This creates a more secure snap connection between the screw and component. Therefore, in a preferred embodiment, the retaining element is a resilient member and the restriction is a rigid structure. In such embodiments the retaining element is deformable from a first diameter to a second, narrower diameter in order to allow passage through the rigid restriction. In other embodiments however it is the restriction which is resilient and distorts from a first diameter to a second, wider diameter in order to allow passage of the rigid retaining element.

The assembly of the present invention can be dimensioned such that, after the retaining element has passed the restriction and entered the first section of the through passage, the resilient member does not return to its rest position but only towards this. In such embodiments a radial force is provided between the screw head and the through passage while the screw is in the retained position. This hinders relative rotation between the screw and secondary component, which can prevent unwanted loosening after the screw has been fastened. However, such rotational resistance also requires a greater amount of torque to be applied to the screw during fastening, which reduces the ease of operation and can damage the screw.

Therefore it is preferable that the assembly is dimensioned such that, after the retaining element has passed through the restriction, the resilient member returns to its first, rest position. This has the effect that, once the screw is retained within the component, no radially acting force is applied between the parts. In a particularly preferred embodiment therefore, when the retaining element forms the resilient member, the first section of the through passage has a diameter greater or equal to the diameter of the retaining element in its rest position. In this way, no radial force is applied to the through passage by the retaining element once this has passed the restriction.

An example of a suitable resilient member is an o-ring or other elastic, compressible component. The use of an elastic component is however less preferred as a screw or dental component comprising an o-ring or other elastic resilient member must necessarily be composed of two separate parts. This increases the cost and complexity of the system. In addition there is the possibility that the o-ring could be displaced and come loose from the screw or secondary component, thus preventing the screw from being correctly retained within the secondary component.

It is therefore preferable that the resilient member is an integral part of the screw or secondary component.

More generally, it is preferable that the retaining element is an integral part of the screw and it is preferable that the restriction is an integral part of the component, regardless of which of these parts forms the resilient member. This simplifies the design and manufacture of the assembly by enabling both the screw and component to be one piece, monolithic structures.

When the retaining element is an integral part of the screw, it is preferable that the retaining element comprises at least one protrusion. The retaining element can comprise a plurality of radial protrusions spaced angularly about the circumference of the screw head, e.g. four protrusions spaced at 90°, three protrusions spaced at 120° or two protrusions spaced at 180° about the longitudinal axis of the screw. However, preferably the retaining element comprises an annular protrusion extending around the circumference of the screw head. Thus, in this embodiment, a single protrusion extends 360° about the longitudinal axis. This form of retaining element is easy to manufacture and is sturdier than multiple, smaller protrusions.

The cross-section of the at least one protrusion, in a plane passing through the longitudinal axis of the screw, can have any shape, e.g. oblong, semi-circular etc. It is preferable however that the cross-section of the at least one protrusion, in a plane of the longitudinal axis of the screw, is barb shaped. A barb is formed by a tapered, curved or otherwise gradated surface which ends in an abrupt step change in diameter such that an abutment surface is formed. This eases the passage of the screw in one direction (i.e. apically) but resists movement in the opposite direction. Thus, when the protrusion is barb-shaped the gradated surface is apically facing.

In embodiments in which the retaining element is a resilient member, the at least one protrusion is preferably flexible in a direction perpendicular to the longitudinal axis of the screw. This enables the protrusion to be flexed towards the longitudinal axis, in order to reduce the diameter of the retaining element and enable this to fit through the restriction.

The retaining element can extend over the axial length of the screw head. In other words, the axial length of the retaining element and screw head can be identical. In such embodiments the entire screw head forms the retaining element. However, preferably the retaining element has an axial length less than that of the screw head. This ensures that the length of the screw head is not restricted by the desired dimensions of the retaining element.

The screw head may further comprise a central depression in its coronal surface. At least a section of this depression may have a non-circular symmetric circumference, such as a hexagonal or Torx® shape. This section can thus be engaged by a screwdriver to rotate the screw. Additionally or alternatively the depression may comprise screw threads. This enables a further component to be fastened to the screw by means of a second screw. When the depression comprises both a non-circular symmetric section and screw threads the screw threads can be located coronal or apical of the non-circular symmetric section but are preferably located coronal of this. This enables the diameter of the screw threads to be wider, which in turn increases the diameter and hence the strength of the screw rod of the second screw.

Furthermore the ability of the non-circular symmetric circumference to withstand torque is increased by positioning this at the apical end of the depression rather than the coronal end.

When the screw head comprises internal screw threads the axial length of the screw head must be great enough to enable a second screw to be firmly fastened to these threads. Consequently, in such embodiments it is particularly beneficial that the axial length of the retaining element is less than the screw head.

In some embodiments the screw head extends coronally of the retaining element, such that in the retained position not all of the screw head is located apically of the restriction. This can be beneficial for example when internal threads are included in the screw head, as in such embodiments the screw head must be relatively long. In such embodiments however it is preferable that the assembly is dimensioned such that, when the screw head abuts the screw seat, the screw head is fully located within the through passage. In other words, the screw does not extend coronally of the secondary component once the screw head abuts the screw seat.

The first section of the through passage, directly apical of the restriction, effectively forms a cavity for housing the retaining element of the screw head. In some embodiments this cavity may be directly coronal of the screw seat, such that the screw seat forms the apical end of the cavity. However, it is not necessary for the first section to be directly coronal of the screw seat, and therefore in other embodiments the cavity may be apically bordered by a second restriction, with the screw seat being located apical of the second restriction. In this second alternative the first section of the through passage must be long enough for the screw head to abut the screw seat prior to the retaining element abutting the second restriction. Thus, in both embodiments it is the abutment of the underside of the screw head against the screw seat which limits the movement of the screw head through the through passage in the apical direction and the retaining element abutting the restriction that prevents the screw from falling out of the coronal end of the screw channel.

The first section of through passage, within which, in the retained position, the retaining element is housed, preferably has a greater axial length than the retaining element. This enables the screw head to move within the through passage while being retained within this. This play between the secondary component and screw is beneficial for seating and fastening the secondary component to the implant.

The second section of the through passage, which forms the restriction, preferably comprises at least one radially inwardly extending protrusion on the surface of the through passage. In some embodiments the second section may comprise a plurality of protrusions angularly spaced about the longitudinal axis of the through passage. Preferably however, the second section comprises an annular protrusion extending about circumference of the through passage. It should be noted that, in embodiments in which the restriction and retaining element are both formed by a plurality of protrusions, the components must be shaped such that the retaining element cannot pass through the restriction simply upon correct rotational alignment of the protrusions. In accordance with the present invention the retaining element can only pass through the restriction when the resilient element is deformed to its second, stressed position.

In some embodiments the at least one protrusion of the second section is flexible in a direction perpendicular to the longitudinal axis of the through passage. However, as discussed above, it is preferable that the restriction is a rigid structure. Therefore in such embodiments the at least one protrusion is inflexible such that the restriction has a fixed diameter.

In order to ease the passage of the retaining element past the restriction, the cross-section of the at least one protrusion of the second section, in a plane passing through the longitudinal axis of the through passage, may be barb shaped, with the gradated surface of the barb being coronally facing. This is particularly beneficial in embodiments in which the at least one protrusion of the retaining element is also barb shaped, with the gradated surface being apically facing. In this way the sloped surfaces contact each other during insertion of the screw head and ease passage of the retaining element through the restriction. Once the retaining element is housed in the cavity however the abutment surfaces of the restriction and retaining element face one another and resist relative coronal movement of the screw. The provision of a barb-shaped retaining element and cooperating barb-shaped restriction is beneficial regardless of which of these elements forms the resilient member.

Preferably the restriction is located directly adjacent to the coronal end of the through passage as this creates the most efficient use of space within the through passage.

The through passage extends from an apical end to a coronal end through the secondary component. The apical end of the through passage will in most instances be located at the apical most end of the secondary component. The coronal end of the through passage is by definition located coronally of the apical end, however it is not necessary for this to be located at the coronal most end of the secondary component. In many instances however the coronal end of the through passage is located at the coronal most end of the component. Furthermore the through passage is usually straight and coaxial with the secondary component. It is however also possible for the through passage to be curved or angled with respect to the longitudinal axis of the secondary component.

The screw seat of the through passage is shaped to abut the underside of the screw head. It can be, e.g., planar, that is, perpendicular to the longitudinal axis of the through passage, or conical. The screw head and screw seat are shaped in a complementary fashion that enables the screw head to be drawn tight against the screw seat, to clamp the component to a dental implant or the like.

The screw rod has a diameter less than that of the screw head and less than all sections of the through passage, such that this can pass unhindered through the passage and protrude from the apical end. The apical end of the screw rod preferably comprises an external thread.

The screw is preferably integrally formed, that is, monolithic.

As defined above, the secondary component is a component which is, in use, directly or indirectly fastened to a dental implant.

The secondary component preferably comprises, at its apical end, implant connection geometry. The implant connection geometry can be designed to connect the component directly or indirectly to the implant. When used in one- or two-part implant systems the component will most usually be designed for direct connection to the implant. However, in other multi-part systems an intermediate component, such as a collar or ring, may be positioned between the implant and the secondary component such that the secondary component connects to this intermediate part or to both the implant and the intermediate part.

The implant connection geometry will usually comprise either a cavity for accommodating an axially protruding boss of the implant system or an apical portion for insertion into an internal bore. In a preferred embodiment the implant connection geometry comprises anti-rotation means for cooperation with implant system anti-rotation means. This could be, for example, a section of the cavity or apical portion having a polygonal cross-section or radially extending grooves or protrusions designed to complement a counterpart anti-rotation means on the implant system boss or internal bore respectively. Many such complementary anti-rotation means for multi-part implant systems are known in the art and any such known means can be employed with the assembly of the present invention.

In a particularly preferred embodiment, the implant connection geometry comprises an apical portion for insertion into an internal bore of an implant. The apical portion preferably comprises an anti-rotation means for co-operation with an implant anti-rotation means. Preferably the apical portion further comprises, coronal of the anti-rotation means, a conical section which tapers radially inwards in the apical direction. The conical section enables an interference fit to be obtained with a complementary conical taper in the internal bore of the implant. This provides a tight seal between the secondary component and implant and prevents incursion of bacteria into the implant.

The secondary component preferably comprises, coronal of the implant connection geometry, a post portion. The post portion extends coronally of the implant connection geometry such that, in use, this extends away from the implant or other part of the implant system that the component is connected to. The post portion can be coaxial to the implant connection geometry or may extend at an angle to this. In some instances the post portion comprises an external surface which is circular symmetric about its longitudinal axis, i.e. the external surface is conical or frusto-conical in shape. In other embodiments however the external surface of the post portion may comprise one or more flat surfaces. Such flat surfaces act as an anti-rotation means on the post portion and enable further components to be attached to the post portion in one or more fixed angular positions. In one particularly preferred embodiment the post portion comprises an anti-rotation section having a polygonal cross-section in a plane perpendicular to the longitudinal axis of the post portion. Preferably the cross-section is octagonal.

Preferably the secondary component further comprises, coronal of the implant connection geometry and apical of the post portion, a coronally facing platform. This platform provides an abutment surface on which a further component can rest, thus forming an axial stop and support. In such embodiments, the post portion extends coronally of the platform, the external surface of the post portion having a diameter less than the platform.

The platform can extend radially in a plane perpendicular to the longitudinal axis of the post portion or at an angle to this, preferably an acute angle such that the platform tapers radially outwards in the coronal direction. This provides a secure stop which can withstand axial forces applied in the apical direction over the lifetime of the secondary component. This is particularly beneficial when the component is an abutment. In other embodiments the platform may taper outwards in the apical direction or take the form of a plurality of discontinuous, stepped surfaces, these surfaces being perpendicular or angled.

The secondary component can be used, for example, as a healing cap. In such embodiments the outer surface of the post portion is shaped to protrude into, and in some cases just through the gingiva and create a natural emergence profile, that is, the external shape of the post portion mimics the external shape of the transgingival portion of a tooth. This enables the gingiva to heal around the healing cap in a shape that will allow a realistically shaped prosthesis to be attached to the implant at a later time. In other embodiments the secondary component may form a part of a multi-part implant, for example an intermediate part such as a collar.

In a preferred embodiment however the secondary component is an abutment. In such embodiments the post portion provides core support to a dental prosthesis. The post portion of the abutment may be co-axial with the longitudinal axis of the implant connection geometry or it may extend at an angle to this. When the secondary component is an abutment it is preferable that the post portion comprises at least one flat surface as discussed above as this enables the prosthesis to be connected to the abutment in a rotationally fixed and defined manner. More generally the external shape of the abutment can take the form of any abutment shape known in the art. The sole requirement is that the abutment shape is capable of supporting a prosthesis which can be glued, cemented, screwed or directly veneered to the abutment. In some embodiments the abutment itself may form the dental prosthesis, that is to say, the exterior of the abutment is shaped to replicate a human tooth or teeth. In these embodiments the prosthesis is integrally formed with the core support of the abutment.

Preferred embodiments of the invention shall now be described, by way of example only, with reference to the accompanying drawings, in which.

Figure 1:
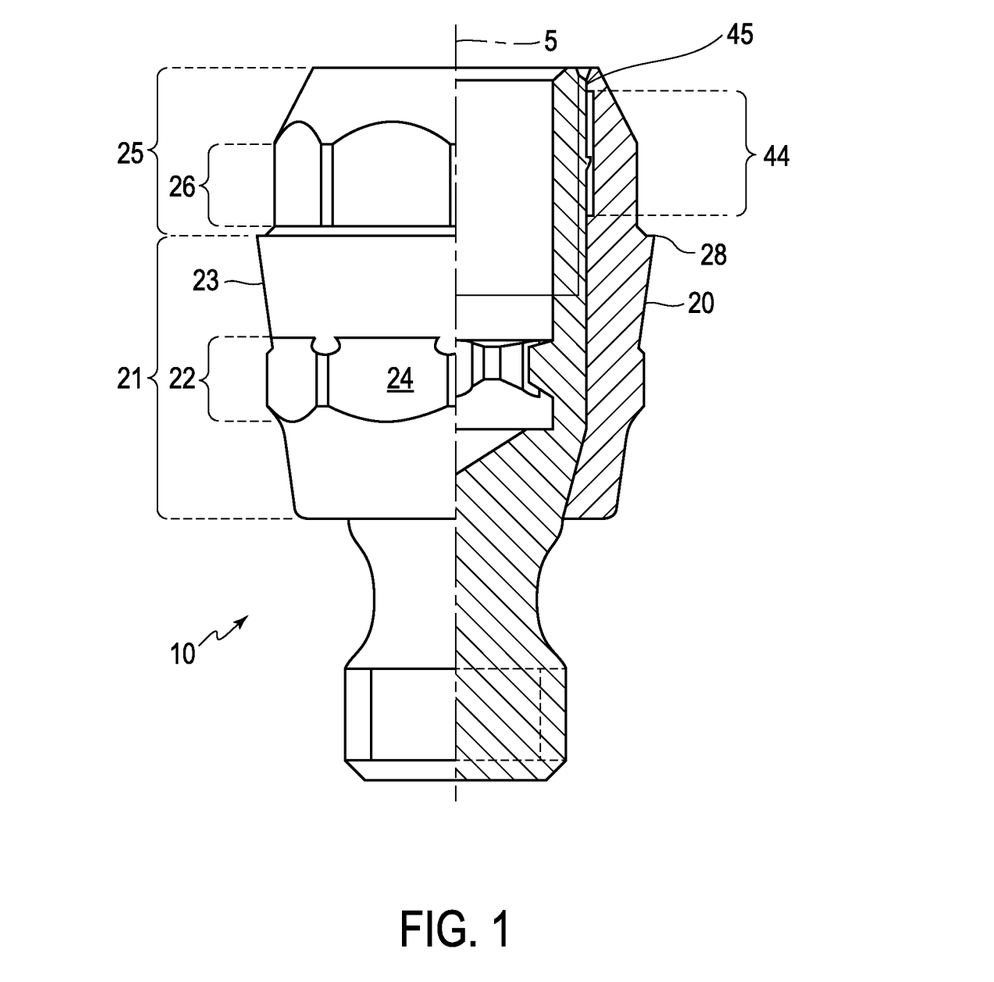
FIG. 1 shows a partial cross-section through a self-retaining screw assembly in accordance with the present invention.

FIG. 1 shows a self-retaining screw assembly 10 in accordance with the present invention. The assembly comprises secondary component 20 and screw 30. In this embodiment secondary component 20 is an abutment for direct connection to a two-part dental implant and is shown in isolation in FIGS. 3, 3A and 3B. It comprises, at its apical end, implant connection geometry 21 for insertion into the internal bore of an implant. The implant connection geometry includes anti-rotation means for forming a rotationally fixed connection to the implant. In the present embodiment the anti-rotation means takes the form of eight flat sides 24 angularly spaced about the longitudinal axis 5 of the abutment, thus forming an octagonal cross-section in a plane perpendicular to this axis. Additionally the implant connection geometry includes a conical section 23 coronal of the anti-rotation means 22 for mating with a complementary conical section of the implant internal bore.

Figure 3:
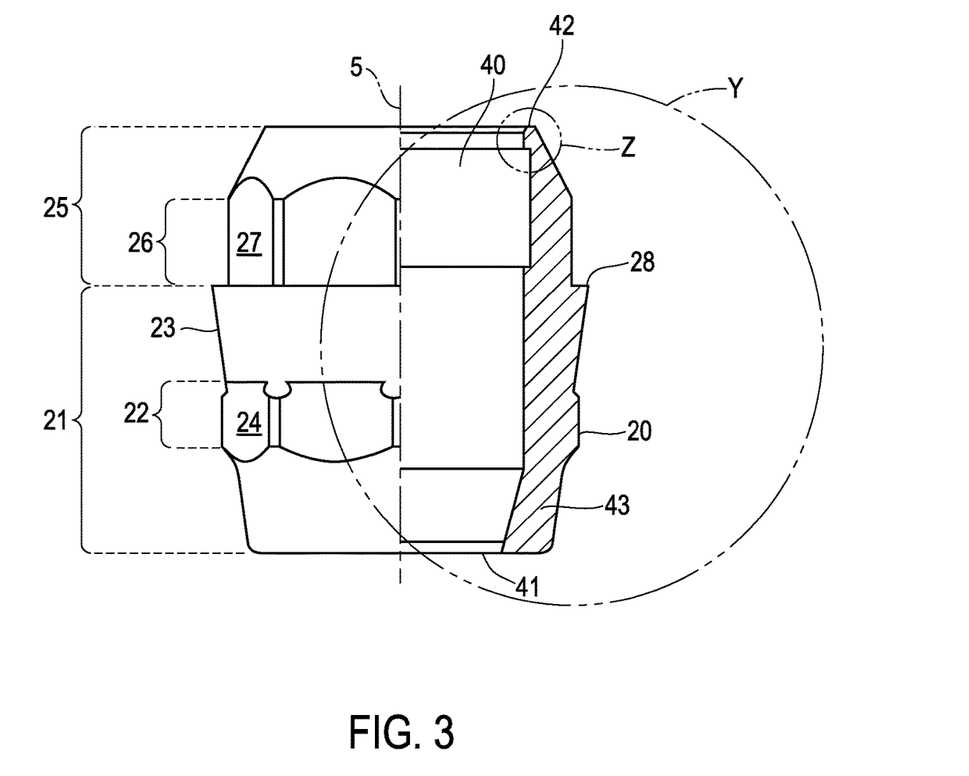
FIG. 3 shows a partial cross-section of the secondary component of the assembly of FIG. 1 in isolation.
Figure 3A:
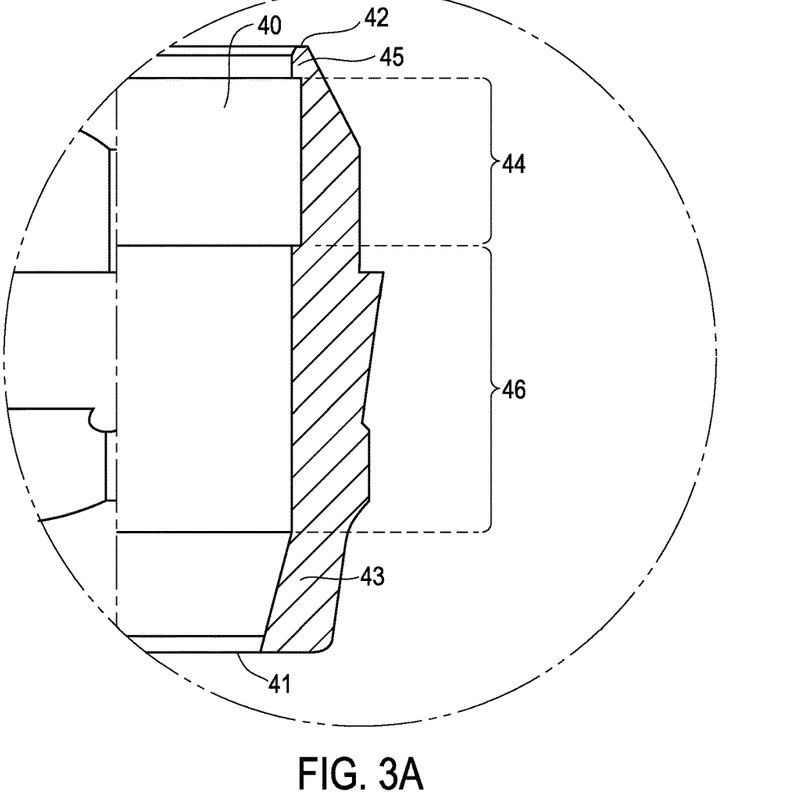
FIG. 3A shows detail Y of FIG. 3.
Figure 3B:
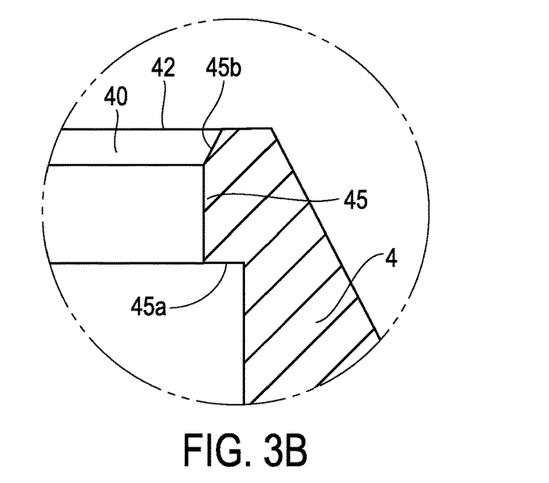
FIG. 3B shows detail Z of FIG. 3.

Conical of the implant connection geometry 21 the abutment comprises a post portion 25 which in use protrudes coronally of the implant and acts as core support to a dental prosthesis. A coronally facing platform 28 is located between the implant connection geometry 21 and post portion 25. In a similar fashion to the implant connection geometry 21, the post portion 25 also comprises an anti-rotation section 26 comprising eight flat surfaces 27 angularly spaced about the longitudinal axis 5 of the abutment, thus forming an octagonal cross-section perpendicular to the longitudinal axis. The anti-rotation section 26 enables a prosthesis to be attached to the abutment in a fixed rotational position. In other embodiments the post portion may only comprise a single flat surface, or it may be circular symmetric. The outer shape of the secondary component does not form part of the inventive concept of the present invention and any known abutment or other secondary component shape may be used.

The secondary component 20 comprises a through passage 40 having an apical open end 41 and a coronal open end 42.

The through passage 40 is coaxial with the secondary component and shaped to accommodate and cooperate with screw 30.

Figure 2:
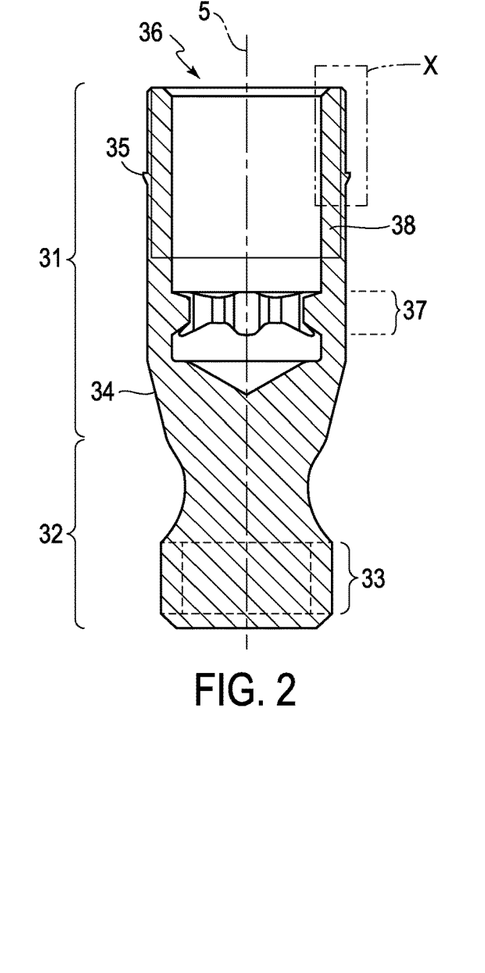
FIG. 2 shows a cross-section of the screw of the assembly of FIG. 1 in isolation.
Figure 2A:
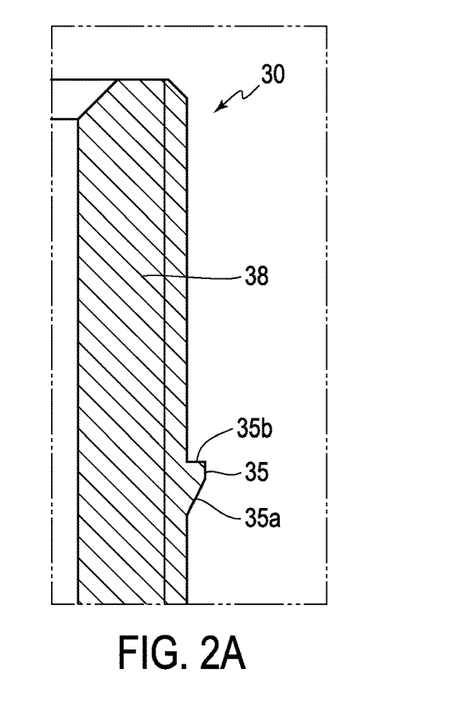
FIG. 2A shows detail X of FIG. 2.

As best seen in FIGS. 2 and 2A, screw 30 comprises a screw head 31 and screw rod 32. Screw rod 32 has an external thread 33 at its apical end and is dimensioned to pass unhindered through the through passage 40 such that this can protrude from the apical end of the passage. Thus the diameter of the screw thread 33 is less than all parts of the through passage 40.

The screw head 31 comprises, at its apical end, a conical surface 34. This surface is dimensioned to abut against screw seat 43 of the through passage 40. Screw seat 43 has a conical shape complementary to the conical surface 34 of the screw head 31 such that the screw head 31 can abut against and be drawn tight against the screw seat 43. In other embodiments, the screw seat and the apical end of the screw head may be planar rather than conical. As the screw head 31 is shaped to abut the screw seat 43 it is not possible for the screw head 31 to pass apically of the screw seat 43.

Coronal of the screw seat 43, the through passage 40 comprises a first section 44 having a first diameter. Directly coronal of first section 44 is a second section having a narrower diameter which thus forms a restriction 45 in the through passage 40. In the present embodiment, the second section of the through passage 40 is formed by an annular protrusion extending around the circumference of the through passage 40. It is to be noted that while the first and second sections of the passage are directly adjacent to one another, in this embodiment first section 44 is not directly coronal of the screw seat 43.

First section 44 forms a cavity within the through passage 40, bordered coronally by restriction 45 and apically by a second restriction 46 formed by a third section of passage having a narrower diameter than first section 44. As can be best seen from FIG. 3B, the apical surface 45a of restriction 45 is a planar surface perpendicular to the longitudinal axis 5 of the through passage 40 whereas the coronal surface 45b is tapered such that the passage widens in the coronal direction.

Screw head 31 comprises, on its external surface, a retaining element 35 in the form of an annular protrusion extending about the circumference of the screw head 31. The protrusion extends radially outwards from the screw head 31 and thus forms the widest part of the screw 30.

As can be seen most clearly from FIG. 2A, the cross-sectional shape of the protrusion, in the plane of the longitudinal axis 1, is barb shaped. The apical surface 35a of retaining element 35 tapers outwards in the coronal direction and the coronal surface 35b is perpendicular to the longitudinal axis of the screw, forming a planar abutment surface. This shape eases passage of the screw in the apical direction and resists movement in the coronal direction.

In the present embodiment the screw head 31 is relatively long in comparison to the overall length of the screw 30. In particular, the screw head 31 is longer than the screw rod 32. The screw head 31 accommodates central depression 36 that extends from the coronal end of the screw into the screw head. This depression comprises a section having a non-circular circumference 37. In other words, the cross-section of this section 37 in a direction perpendicular to the longitudinal axis 1 of the screw 30 is non-circular.

The non-circular circumference enables the depression 36 to be engaged by a screwdriver in order to impart torque to the screw 30 and rotate this. Additionally in the present embodiment the depression 36 comprises an internal screw thread 38. This enables an additional constituent of the dental implant system to be connected to the screw 30 by means of a further screw, in a similar manner to that shown in, e.g. U.S. Pat. No. 4,850,870. In embodiments in which no internal thread 38 is present in the screw head 31 the length of the screw head will normally be shorter.

The secondary component 20 and screw 30 are designed such that the first section 44 of the through passage 40 has a diameter which is greater than the diameter of the retaining element 35 while the restriction 45 has a diameter less than the diameter of the retaining element 35.

Figure 4:
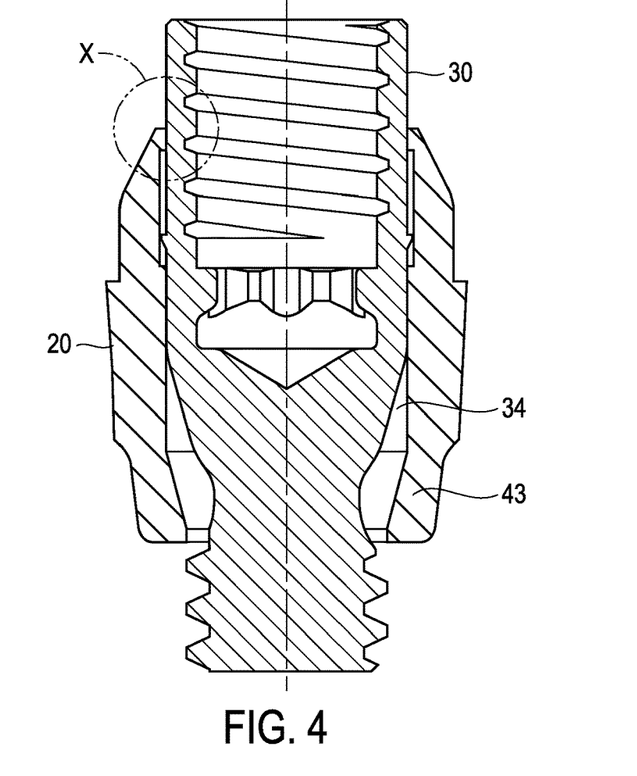
FIG. 4 shows the assembly of FIG. 1 with the screw in an unretained position relative to the secondary component.
Figure 4A:
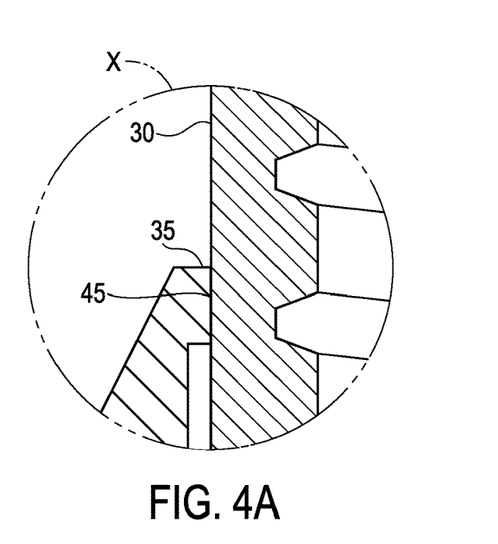
FIG. 4A shows detail X of FIG. 4.

When the screw 30 is first inserted into the coronal end of the through passage 40 therefore the retaining element 35 rests on the restriction 45, as can be seen in FIGS. 4 and 4A. The retaining element 35 is however resilient such that it can be deformed to a stressed position in which its diameter is smaller than when in its rest position. Thus, when a directed force is applied to the screw head the retaining element 35 flexes and is forced past restriction 45. The tapered apical surface 35a of the retaining element 35 and tapered coronal surface 45b of the restriction 45 cooperate to ease passage of the retaining element 35 through the restriction 45 by assisting the movement of the retaining element into its stressed position. Once past the restriction 45 the retaining element 35 enters the first section 44, with its greater diameter, which allows the retaining element 35 to return to its rest position.

The retaining element 35 is thus housed in the first section 44 of the passage 40. Once within this cavity it is not possible for the retaining element 35 to pass back through the restriction 45 unless this is once again forced into its stressed position. The planar coronal surface 35b of the retaining element 35 and apical surface 45a of the restriction 45 abut against one another and resist inward flexing of the retaining element 35.

As discussed previously, the apical conical surface 34 of the screw head 31 is shaped to abut the screw seat 43 and therefore cannot pass apically beyond this. The screw 30 is therefore retained within the secondary component 20.

As can be seen from FIG. 1 the length of the first section 44 of the through passage 40 is greater than that of retaining element 35. This enables the screw 30 to have some axial play within the component 20.

Figure 5A:
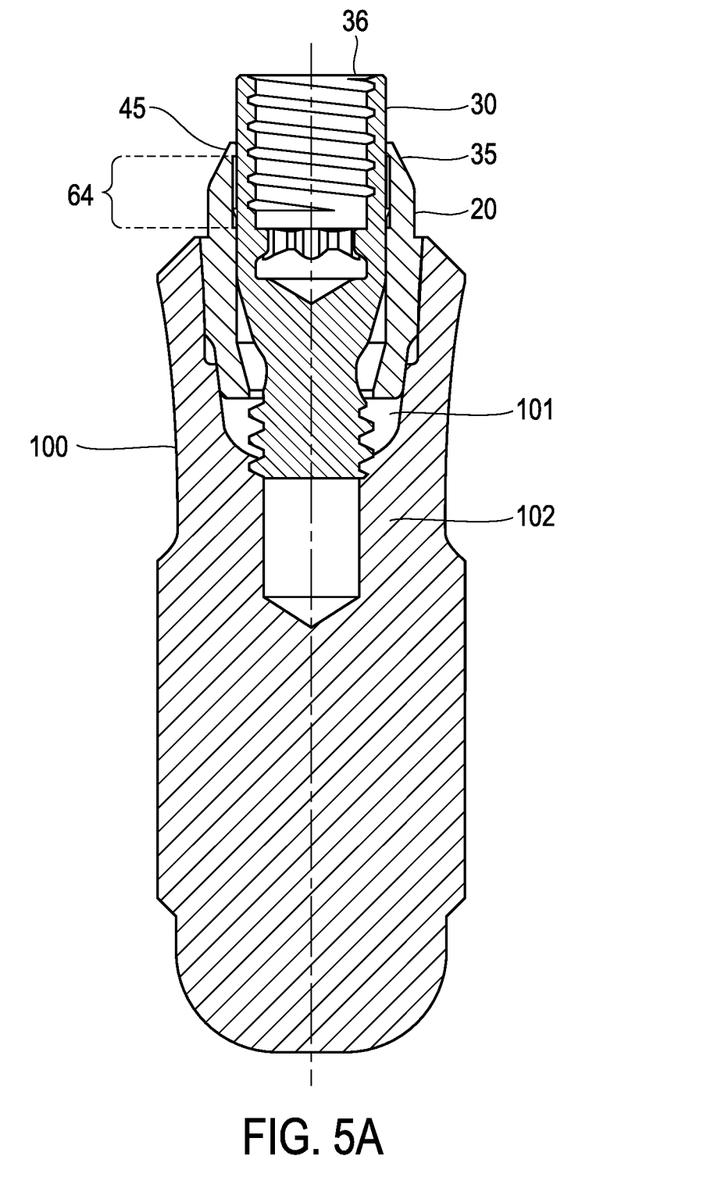
FIG. 5A shows the assembly of FIG. 1 with the screw retained within the component in combination with a dental implant.

FIG. 5A shows the assembly 10 in combination with a dental implant 100 of a two-part implant system. The implant 100 comprises an internal bore 101 extending from the coronal end of the implant. The external features of the implant are not relevant to the present invention but may comprise a threaded region.

The internal bore 101 is shaped to house the implant connection geometry 21 of the secondary component. It therefore comprises a conical section complementary to conical section 23 of the abutment and an anti-rotation means that engages in a non-rotational manner with anti-rotation means 22. Apical of these features the internal bore 101 comprises an internal thread 102.

Figure 5B:
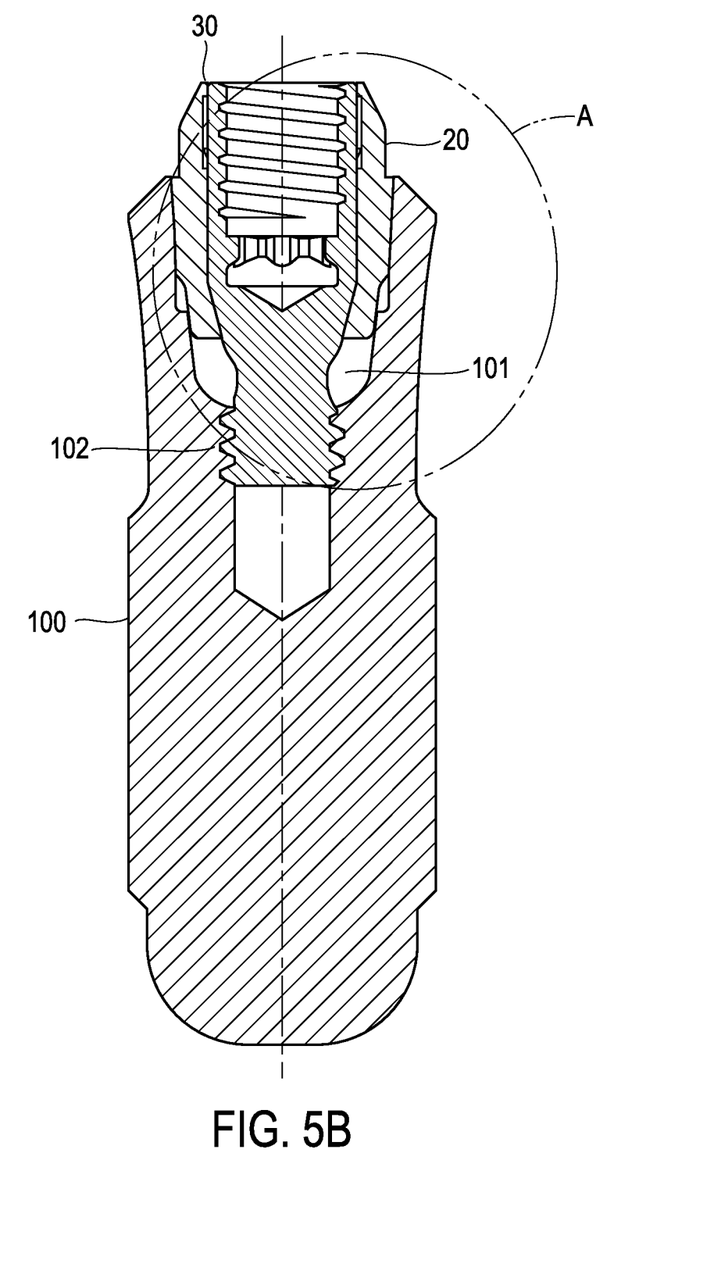
FIG. 5B shows the combination of FIG. 5B with the screw fastened to the implant.
Figure 5C:
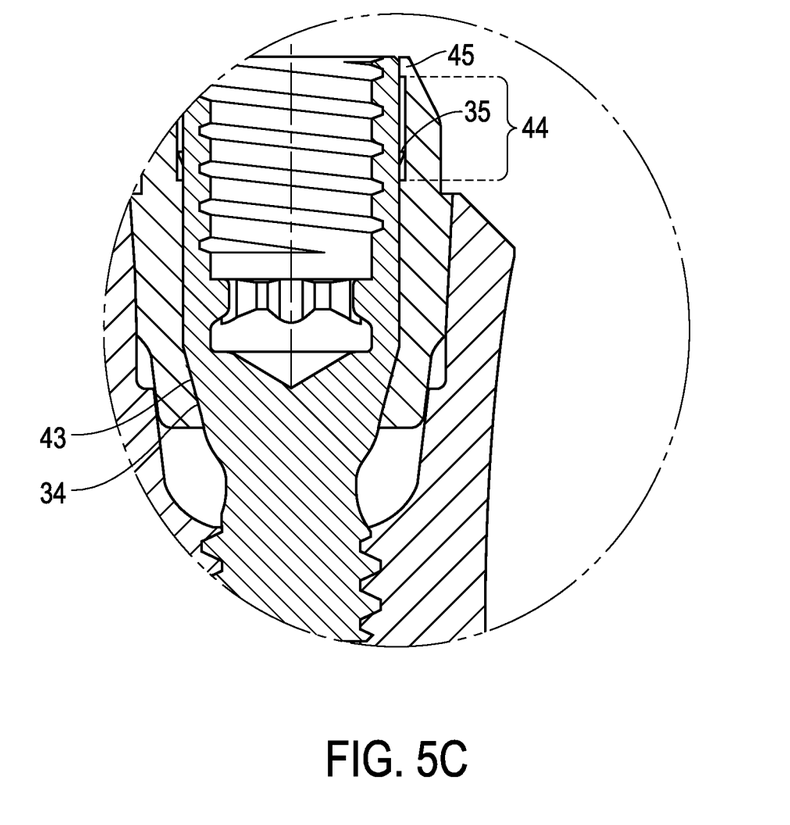
FIG. 5C shows detail A of FIG. 5B.

In FIG. 5A the abutment is fully seated within the internal bore 101 of the implant 100, that is, the respective conical and anti-rotation sections are aligned. The screw is not yet fastened to the implant thread 102. The retaining element 35 is located at the coronal end of the first section 44, however it is prevented from moving higher within the passage 40 by restriction 45. By inserting a suitable screwdriver into the central depression 36 and engaging non-circular section 37 the thread 33 of the screw rod 32 engages the implant thread 102 and thus draws the screw 30 downwards in the apical direction such that the conical surface 34 of the screw head 31 abuts the screw seat 43 and clamps the abutment to the implant 100. This can be seen in FIGS. 5B and 5C. Once the screw head 31 abuts against the screw seat 43 all of the screw head 31 is located within the through passage 40. As is most clearly seen in FIG. 5C, the retaining element 35 is located at a position remote from the apical end of the first section 44 and hence does not interfere with the engagement between the screw seat 43 and the screw head 31.

The above described embodiments are for illustrative purposes only and the skilled man will realize that many alternative arrangements are possible which fall within the scope of the claims. In particular, the retaining element and restriction may have different shapes and may comprise multiple, angularly spaced protrusions. The screw head may not comprise an internal thread. In other embodiments the restriction may form the resilient member and distort to a wider diameter in order to allow passage of the retaining element.

Where technical features mentioned in any claim are followed by reference signs, those reference signs have been included just for the sole purpose of increasing intelligibility of the claims and accordingly, such reference signs do not have any limiting effect on the scope of each element identified by way of example by such reference signs.

The invention claimed is:

1. A self-retaining screw assembly comprising
a dental secondary component and
a screw,
the secondary component comprising
   a through passage having an apical and a coronal open end, and
   a screw seat located between said apical and coronal ends,
the screw comprising
   a screw rod and
   a screw head,
the screw head being dimensioned to abut against the screw seat and the screw rod being dimensioned to pass unhindered through the through passage such that the apical end of the rod can protrude from the apical end of the through passage,
the through passage further comprising,
   coronal of the screw seat, a first section and,
   directly coronal of the first section a second section having a narrower diameter than the first section, such that the second section forms a restriction in the through passage and
the screw head comprising a radially outwardly extending retaining element,
at least one of the restriction and retaining element being a resilient member deformable from a first, rest, position, in which the resilient member has a first diameter, to a second, stressed, position, in which the resilient member has a second diameter,
the restriction and the retaining element being dimensioned such that the retaining element can only pass through the restriction when the resilient member is in the stressed position,
the resilient member being an integral part of the screw or secondary component,
the retaining element of the screw head is located at a position axially remote from an apical side of the screw head that abuts against the screw seat,
the retaining element is an integral part of the screw and comprises at least one protrusion, and
the cross-section of the at least one protrusion in a plane of the longitudinal axis of the screw is barb shaped.

2. An assembly as claimed in claim 1, wherein at least the retaining element is a resilient member deformable from the first, rest, position having the first diameter to the second, stressed, position having the second diameter, the retaining element and restriction being dimensioned such that the retaining element can only pass through the restriction when in the second position.

3. An assembly as claimed in claim 2, wherein the assembly is dimensioned such that, after the retaining element has passed through the restriction, the resilient member returns to its first, rest position.

4. An assembly as claimed in claim 3, wherein the first section of the through passage has a diameter greater or equal to the diameter of the retaining element in its rest position.

5. An assembly as claimed in claim 1, wherein the retaining element is a resilient member and the restriction is a rigid structure.

6. An assembly as claimed in claim 1, wherein the retaining element comprises an annular protrusion extending around the circumference of the screw head.

7. An assembly as claimed in claim 1, wherein the at least one protrusion is flexible in a direction perpendicular to the longitudinal axis of the screw.

8. An assembly as claimed in claim 1, wherein the screw is monolithic.

9. An assembly as claimed in claim 1, wherein the secondary component and screw are both one piece, monolithic structures.

10. An assembly as claimed in claim 1, wherein the retaining element has an axial length less than that of the screw head.

11. An assembly as claimed in claim 1, wherein the second section of the through passage comprises at least one radially inwardly extending protrusion on the surface of the through passage.

12. An assembly as claimed in claim 11, wherein the cross-section of the at least one protrusion of the second section, in a plane passing through the longitudinal axis of the through passage, is barb shaped with the gradated surface of the barb being coronally facing.

13. An assembly as claimed in claim 1, wherein the secondary component is an abutment.

\* \* \* \* \*